United States Patent
Holowecky et al.

(10) Patent No.: US 10,849,734 B2
(45) Date of Patent: Dec. 1, 2020

(54) METHODS OF TISSUE REPAIRS

(71) Applicant: ARTHREX, INC., Naples, FL (US)

(72) Inventors: Allen E. Holowecky, Naples, FL (US); Loren D. Crook, Estero, FL (US)

(73) Assignee: ARTHREX, INC., Naples, FL (US)

( * ) Notice: Subject to any disclaimer, the term of this patent is extended or adjusted under 35 U.S.C. 154(b) by 114 days.

(21) Appl. No.: 15/998,516

(22) Filed: Aug. 16, 2018

(65) Prior Publication Data

US 2020/0054439 A1 Feb. 20, 2020

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0459* (2013.01); *A61F 2002/0829* (2013.01); *A61F 2002/0858* (2013.01)

(58) Field of Classification Search
CPC ...... A61F 2002/0852; A61F 2002/0847; A61F 2002/0858; A61F 2002/0864; A61F 2002/0829; A61B 17/0401; A61B 2017/0459; A61B 2017/0469; A61B 2017/0458; A61B 17/0485; A61B 2017/0462; A61B 2017/0485; A61B 2017/0496; A61B 2017/06057; A61B 2017/06052
See application file for complete search history.

(56) References Cited

U.S. PATENT DOCUMENTS

| | | | |
|---|---|---|---|
| 6,045,574 A | 4/2000 | Thal | |
| 6,143,017 A | 11/2000 | Thal | |
| 6,296,659 B1 | 10/2001 | Foerster | |
| 6,511,498 B1 | 1/2003 | Fumex | |
| 6,544,281 B2 | 4/2003 | ElAttrache et al. | |
| 7,285,124 B2 | 10/2007 | Foerster | |
| 7,749,250 B2 | 7/2010 | Stone et al. | |
| 7,857,830 B2 * | 12/2010 | Stone | A61B 17/0469 606/232 |
| 7,905,903 B2 * | 3/2011 | Stone | A61B 17/0401 606/232 |
| 7,905,904 B2 | 3/2011 | Stone et al. | |
| 7,909,851 B2 | 3/2011 | Stone et al. | |
| 7,959,650 B2 * | 6/2011 | Kaiser | A61F 2/0811 606/232 |
| 8,088,130 B2 * | 1/2012 | Kaiser | A61B 17/0401 606/139 |
| 8,118,836 B2 * | 2/2012 | Denham | A61B 17/06166 606/232 |

(Continued)

*Primary Examiner* — Alvin J Stewart
(74) *Attorney, Agent, or Firm* — Potomac Law Group PLLC

(57) ABSTRACT

Surgical constructs and methods of soft tissue repairs. A tendon is approximated to bone with a surgical construct in the form of a soft anchor that includes a soft anchor sheath and shuttling sutures passed through the soft anchor sheath. The soft anchor sheath loaded with the shuttling sutures is inserted either unicortically or bicortically. Suture limbs extending from sutured tendon are passed/shuttled through the sheath by employing the shuttling sutures. The tendon is secured into or onto the bone. The suture limbs may be passed through the soft anchor sheath in various directions and/or orientations and/or locations.

13 Claims, 8 Drawing Sheets

(56) References Cited

U.S. PATENT DOCUMENTS

| | | | |
|---|---|---|---|
| 8,231,654 B2 | 7/2012 | Kaiser et al. | |
| 8,273,106 B2 | 9/2012 | Stone et al. | |
| 8,298,262 B2 | 10/2012 | Stone et al. | |
| 8,303,604 B2 | 11/2012 | Stone et al. | |
| 8,361,113 B2 | 1/2013 | Stone et al. | |
| 8,545,535 B2 | 10/2013 | Hirotsuka et al. | |
| 8,562,645 B2 | 10/2013 | Stone et al. | |
| 8,562,647 B2 | 10/2013 | Kaiser et al. | |
| 8,574,235 B2 | 11/2013 | Stone | |
| 8,597,327 B2 | 12/2013 | Stone et al. | |
| 8,608,777 B2 | 12/2013 | Kaiser et al. | |
| 8,652,172 B2 | 2/2014 | Denham et al. | |
| 8,672,968 B2 | 3/2014 | Stone et al. | |
| 8,840,645 B2 | 9/2014 | Denham et al. | |
| 8,936,621 B2 * | 1/2015 | Denham | A61F 2/0811 606/232 |
| 9,005,287 B2 | 4/2015 | Stone | |
| 9,095,331 B2 | 8/2015 | Hernandez et al. | |
| 9,149,267 B2 | 10/2015 | Norton et al. | |
| 9,198,653 B2 | 12/2015 | Sengun et al. | |
| 9,198,656 B1 * | 12/2015 | Ferguson | A61B 17/0485 |
| 9,271,713 B2 | 3/2016 | Denham et al. | |
| 9,314,241 B2 | 4/2016 | Stone et al. | |
| 9,345,567 B2 | 5/2016 | Sengun | |
| 9,357,992 B2 | 6/2016 | Stone et al. | |
| 9,370,350 B2 | 6/2016 | Norton | |
| 9,402,621 B2 | 8/2016 | Stone et al. | |
| 9,463,013 B2 | 10/2016 | Pilgeram et al. | |
| 9,492,158 B2 | 11/2016 | Stone et al. | |
| 9,498,204 B2 | 11/2016 | Denham et al. | |
| 9,504,460 B2 | 11/2016 | Stone et al. | |
| 9,510,821 B2 | 12/2016 | Denham et al. | |
| 9,532,777 B2 | 1/2017 | Kaiser et al. | |
| 9,539,000 B2 | 1/2017 | Hendricksen et al. | |
| 9,539,003 B2 | 1/2017 | Stone et al. | |
| 9,603,591 B2 | 3/2017 | Denham et al. | |
| 9,622,736 B2 | 4/2017 | Stone et al. | |
| 9,788,826 B2 * | 10/2017 | McCartney | A61B 17/0401 |
| 9,801,708 B2 | 10/2017 | Denham et al. | |
| 9,974,534 B2 | 5/2018 | Troxel et al. | |
| 10,034,663 B1 * | 7/2018 | Nason | A61B 17/0401 |
| 10,070,856 B1 * | 9/2018 | Black | A61B 17/0401 |
| 10,610,212 B2 | 4/2020 | Breslich | |
| 10,610,217 B2 | 4/2020 | Stone et al. | |
| 2003/0130694 A1 * | 7/2003 | Bojarski | A61F 2/0805 606/228 |
| 2005/0049635 A1 * | 3/2005 | Leiboff | A61B 17/0401 606/213 |
| 2008/0065114 A1 * | 3/2008 | Stone | A61B 17/0401 606/139 |
| 2009/0105754 A1 | 4/2009 | Sethi | |
| 2010/0268273 A1 * | 10/2010 | Albertorio | A61B 17/0401 606/232 |
| 2012/0046693 A1 * | 2/2012 | Denham | A61B 17/0401 606/232 |
| 2013/0096611 A1 * | 4/2013 | Sullivan | A61B 17/0485 606/232 |
| 2013/0116730 A1 * | 5/2013 | Denham | A61B 17/0401 606/232 |
| 2013/0296895 A1 * | 11/2013 | Sengun | A61B 17/0401 606/148 |
| 2013/0296934 A1 * | 11/2013 | Sengun | A61B 17/06166 606/232 |
| 2014/0249577 A1 * | 9/2014 | Pilgeram | A61B 17/0485 606/228 |
| 2015/0142050 A1 * | 5/2015 | Ferguson | A61B 17/0485 606/228 |
| 2015/0164497 A1 * | 6/2015 | Callison | A61B 17/0485 606/232 |
| 2015/0173739 A1 * | 6/2015 | Rodriguez | A61B 17/0401 606/232 |
| 2015/0173754 A1 * | 6/2015 | Norton | A61B 17/0487 606/228 |
| 2016/0058436 A1 * | 3/2016 | Stone | A61B 17/0482 606/232 |
| 2016/0113642 A1 * | 4/2016 | Pilgeram | A61B 17/0401 606/232 |
| 2017/0014225 A1 * | 1/2017 | Denham | A61F 2/0811 |
| 2017/0049432 A1 * | 2/2017 | Dooney, Jr. | A61B 17/0487 |
| 2017/0049434 A1 * | 2/2017 | Dooney, Jr. | A61B 17/0485 |
| 2017/0119382 A1 * | 5/2017 | Denham | A61F 2/0811 |
| 2017/0189007 A1 * | 7/2017 | Burkhart | A61B 17/0485 |
| 2017/0311947 A1 | 11/2017 | Kaiser et al. | |
| 2017/0360437 A1 * | 12/2017 | Ferguson | A61F 2/08 |
| 2019/0038276 A1 * | 2/2019 | Jackson | A61B 17/0401 |
| 2019/0247039 A1 * | 8/2019 | Gregoire | A61F 2/0811 |
| 2019/0274681 A1 * | 9/2019 | Denham | A61B 17/06166 |
| 2019/0290258 A1 * | 9/2019 | Denham | A61B 17/0487 |
| 2019/0314143 A1 * | 10/2019 | Jackson | A61B 17/0401 |
| 2019/0358023 A1 * | 11/2019 | Winter | A61F 2/08 |

* cited by examiner

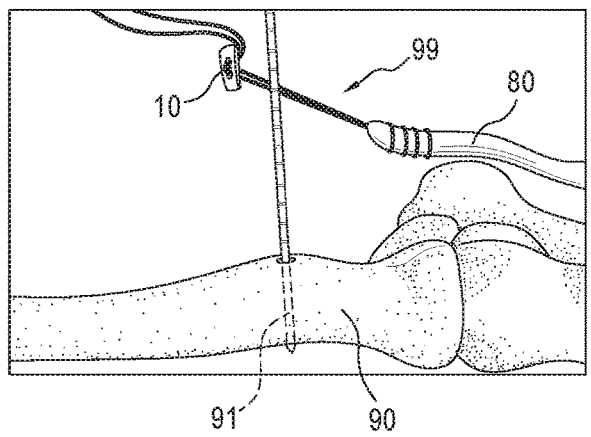
FIG. 5
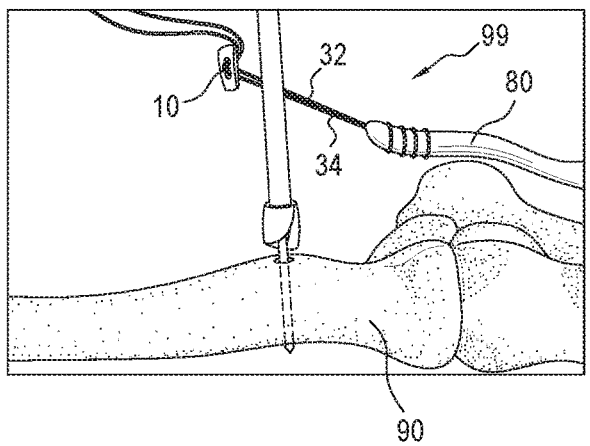
FIG. 6
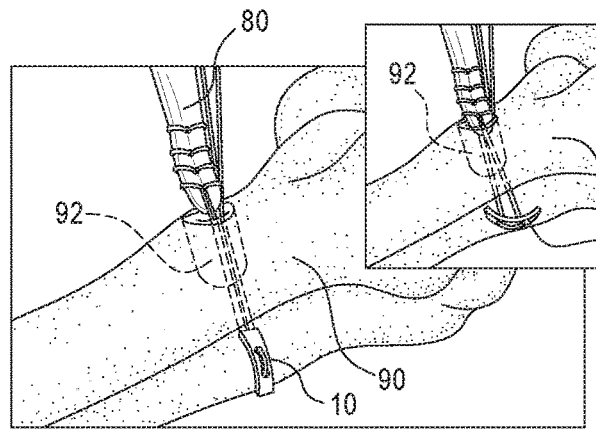
FIG. 7
FIG. 8
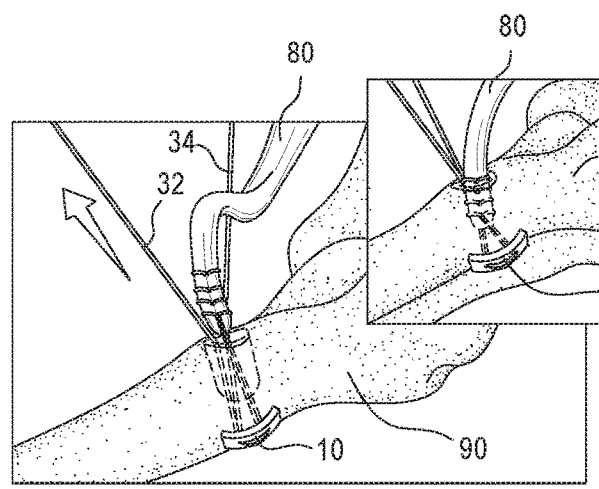
FIG. 9
FIG. 10

METHODS OF TISSUE REPAIRS

BACKGROUND

The disclosure relates to the field of surgery and, more specifically, to tissue repairs for reconstructive surgeries.

SUMMARY

Reconstruction systems, assemblies, kits and methods of tissue repairs are disclosed.

A tendon-slide technique is employed to repair distal tendon ruptures with a soft anchor. A tendon is approximated to bone with a surgical construct in the form of a soft anchor that includes a sheath and a tensionable construct attached to the sheath. In an embodiment, shuttling sutures are passed through a soft anchor sheath. The soft anchor sheath loaded with the shuttling sutures is inserted either unicortically or bicortically. Suture limbs extending from sutured tendon are passed/shuttled through the sheath by employing the shuttling sutures. The tendon is secured into or onto the bone. The suture limbs may be passed through the soft anchor sheath in various directions and/or orientations and/or locations.

BRIEF DESCRIPTION OF THE DRAWINGS

FIGS. 3-13 illustrate a tension-slide technique according to an exemplary embodiment.

DETAILED DESCRIPTION

Figure 1:
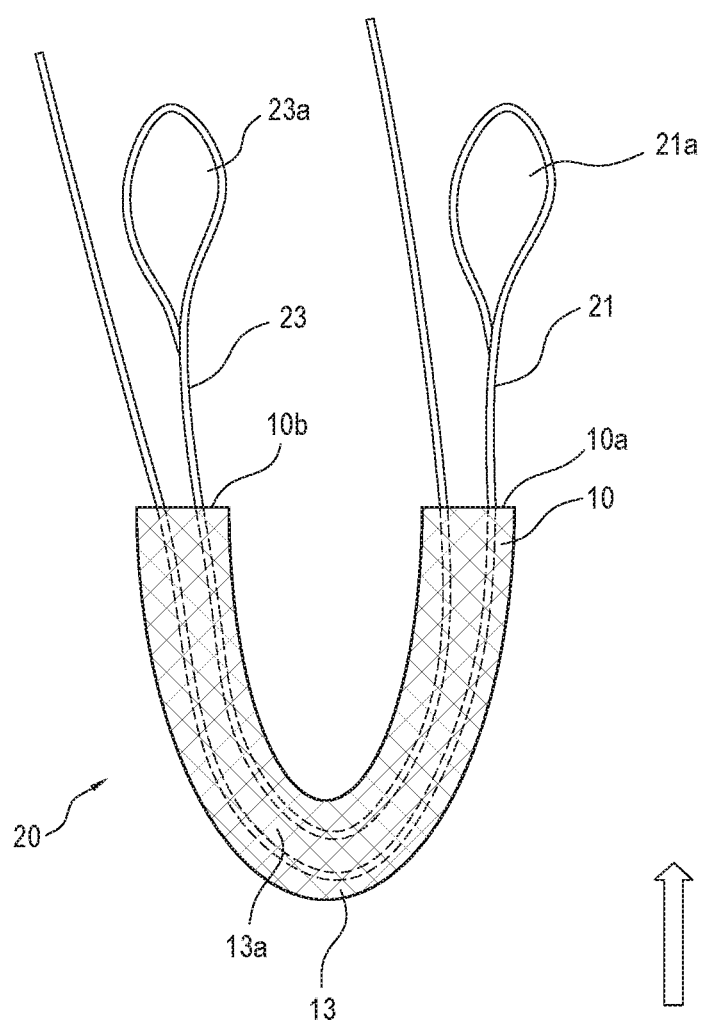
FIG. 1 illustrates a surgical construct according to an exemplary embodiment.

The disclosure provides surgical systems, assemblies, constructs, kits and methods for securing soft tissue to bone with a tensionable construct.

In an embodiment, a surgical construct is a soft anchor in the form of a soft anchor sleeve (sheath) attached to soft tissue (e.g., tendon, ligament, etc.) to be positioned relative to bone. The surgical construct may be a single-loaded construct or multiple-loaded construct (multiple-tail construct). In an embodiment, the sleeve is attached to soft tissue by one or more flexible strands that are sutured/fixed to the soft tissue. The soft anchor sleeve (sheath) may be secured within a second tissue (for example, bone) and the tensionable construct may secure the soft tissue to the second tissue. The construct may be knotted or knotless.

In an embodiment, a surgical construct is a soft anchor that includes a soft anchor sleeve (sheath) and a tensionable construct with at least two flexible strands extending through the soft anchor sleeve (sheath). In an embodiment, a surgical construct includes a soft anchor sleeve (sheath) and at least two flexible strands extending through at least one passage/cannulation of the soft anchor sleeve. The at least two flexible strands may extend through the sleeve in similar or different directions and/or orientations and/or locations. The at least two flexible strands may extend through the sleeve in opposite directions. The at least two flexible strands are attached to the soft tissue, for example, securely attached to it. The at least two flexible strands may be sutured, for example, whipstitched, to soft tissue (e.g., tendon) to be secured to bone.

In an embodiment, a surgical construct is a soft anchor that includes a soft anchor sleeve (sheath) in the form of a tubular member with a first end and a second end; and a tensionable construct attached to the soft anchor sleeve (sheath). The tensionable construct may include one or more flexible strands extending through the soft anchor sleeve and secured to a tendon. At least one of the first and second ends may be an open end. The flexible strands may extend through the sleeve in similar or different directions and/or orientations and/or locations. The surgical construct may include one or more shuttling devices (passing devices or shuttle/pull devices or shuttling sutures) attached to the soft anchor sleeve and employed to shuttle/pass the flexible strands through the sleeve at different locations and/or orientations and/or directions. The shuttling devices may be shuttling wires or sliding shuttle stitches or any suture passing devices. The shuttling devices may be loaded with the flexible strands.

In an embodiment, a surgical construct is a soft anchor in the form of a multiple-loaded construct (multiple-loop construct or multiple-tail construct). The construct includes a soft anchor sleeve (sheath); a first flexible strand extending through a first passage of the soft anchor sleeve in a first direction; and a second flexible strand extending through a second passage of the soft anchor sleeve in a second direction, which may be similar or different from the first direction. The first and second flexible strands are attached to soft tissue to be positioned relative to bone. The soft anchor sleeve may be secured into or onto bone and the tensionable construct may secure the soft tissue (for example, distal biceps tendon) to the bone. The first direction may be opposite the second direction. The first and second directions may extend about parallel to a longitudinal axis of the sheath. The first and second directions may extend about parallel to a transversal axis of the sheath. The first and second flexible strands may extend for a first length or portion about parallel to a longitudinal axis of the sheath, and for a second length or portion about parallel to a transversal axis of the sheath. The construct may further include additional flexible strands. The first and second passages may be concentrically located and/or may extend in various directions relative to each other.

Methods of tissue repair are also disclosed. In an embodiment, a method of tissue repair comprises inter alia (i) providing a soft flexible sleeve (soft anchor sleeve, tubular member, or sheath) with two shuttling strands passing through the flexible sleeve and in a first and second direction, respectively; (ii) securing the flexible sleeve with the two shuttling strands into or onto bone; (iii) passing suturing strands from a sutured soft tissue through the flexible sleeve by employing the two shuttling strands to shuttle the suturing strands through the flexible sleeve; and (iv) pulling on the suturing strands to approximate the sutured soft tissue to bone. The first direction may be similar to, or different from, the second direction. The first direction may be opposite the second direction. The first and second directions may be about parallel to a longitudinal axis of the sheath. The suturing strands may extend about parallel to a longitudinal axis of the sleeve, or about parallel to a transversal axis of the sheath, or in any directions (similar or different) relative to the two axis of the sleeve. The suturing strands may extend about parallel to a longitudinal axis of the sleeve for a first length or portion and then may extend about parallel to a transversal axis of the sheath, exiting the sheath at about a 90 degree angle with the longitudinal axis of the sheath.

In an embodiment, a method of distal biceps repair using a soft loadable button and tension-slide technique is conducted by inter alia (i) securing a soft button in the form of a flexible sleeve (soft anchor sleeve, tubular member, or sheath) into or onto bone, the flexible sleeve further including two shuttling strands passing through a length of the flexible sleeve and in opposite directions; and (ii) passing suturing strands from a sutured distal tendon through the flexible sleeve, by employing the two shuttling strands to shuttle the suturing strands through the flexible sleeve. The method further includes (iii) pulling on the suturing strands to approximate and secure the distal biceps tendon to bone. Step (ii) may be conducted before or after step (i).

The surgical constructs and methods of the present disclosure provide apparatus, systems, assemblies, kits and methods for tissue repair, for example, distal biceps repair using a loadable soft button and tension-slide technique. The methods of the present disclosure provide surgeons with a non-metallic button option which will not be visible on X-rays and which allows surgeons to drill a smaller tunnel than those required for metal buttons. The disclosure provides a "cortical" soft button that is preloaded with shuttling devices (shuttling FiberLink™ sutures with a closed loop on one end, for example) to enable to attach external sutures to the soft anchor/button.

As detailed below, during a biceps tenodesis, for example, a soft flexible sheath is preloaded with shuttling sutures (wire loops) so that each loop of a shuttling suture extends at an end opposite the other end. External sutures are shuttled through the sheath in various directions (by employing the shuttling sutures). In this manner, whipstitched suture limbs (sutured to a distal tendon) are shuttled through the sheath using the shuttling sutures (for example, FiberLink™ sutures). The tendon will tension slide into or onto the bone. The technique requires a smaller drill hole and the final repair (loadable soft button) does not show up on X-rays.

The present disclosure also provides systems, assemblies and kits containing implants, drill(s), guide, FiberLoop® sutures and free needle. The implants/constructs of the disclosure may be available alone or in combination with other elements, i.e., part of kits, systems, etc.

Figure 14:
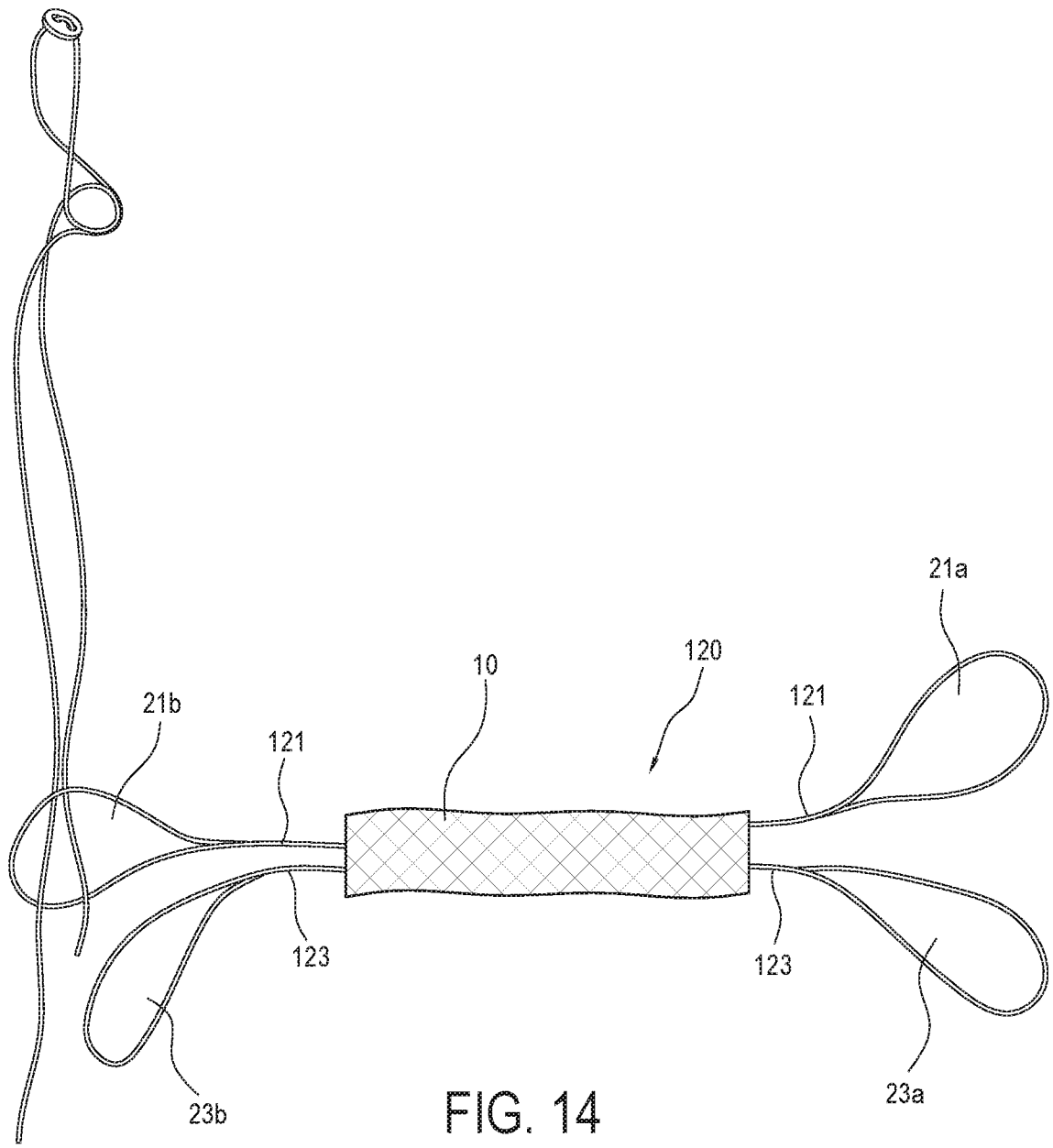
FIG. 14 illustrates a surgical construct according to another exemplary embodiment.
Figure 15:
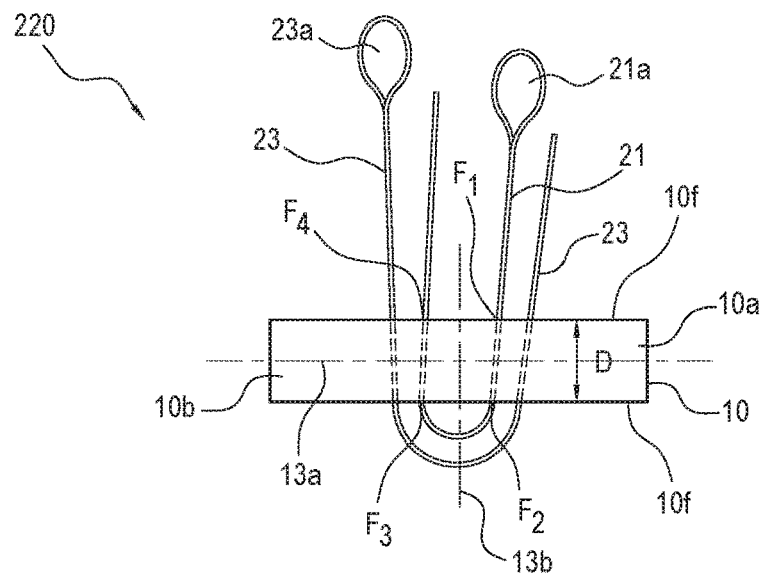
FIG. 15 illustrates a surgical construct according to another exemplary embodiment.
Figure 16:
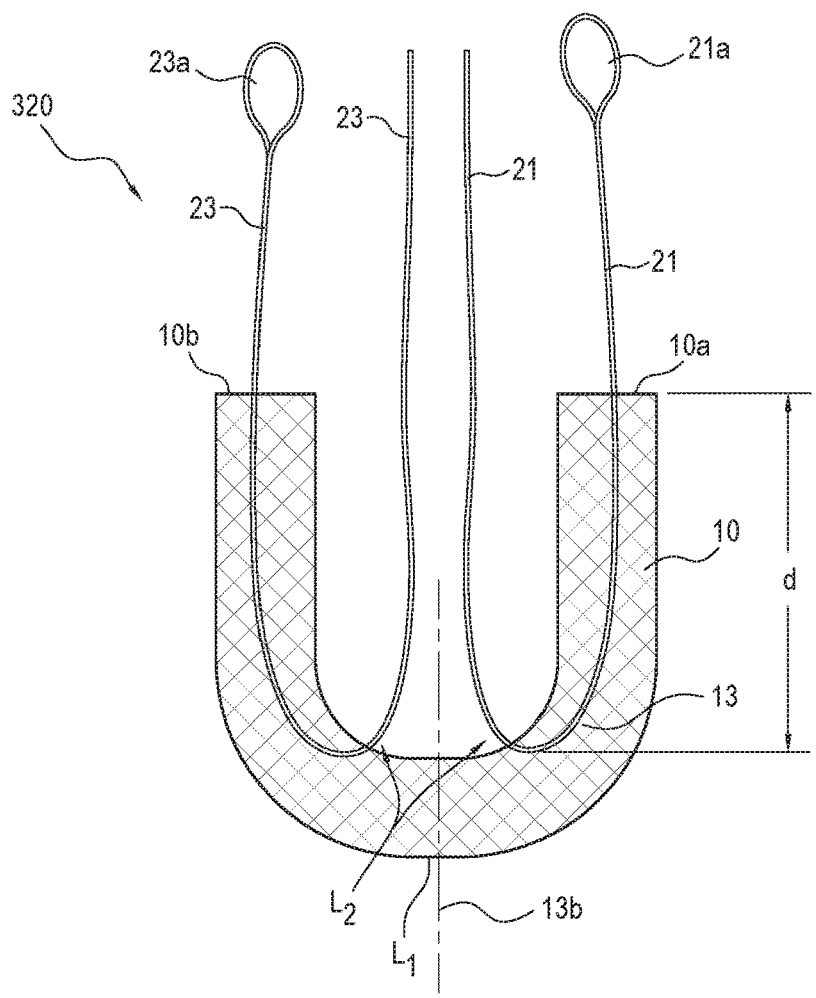
FIG. 16 illustrates a surgical construct according to another exemplary embodiment.
Figure 17:
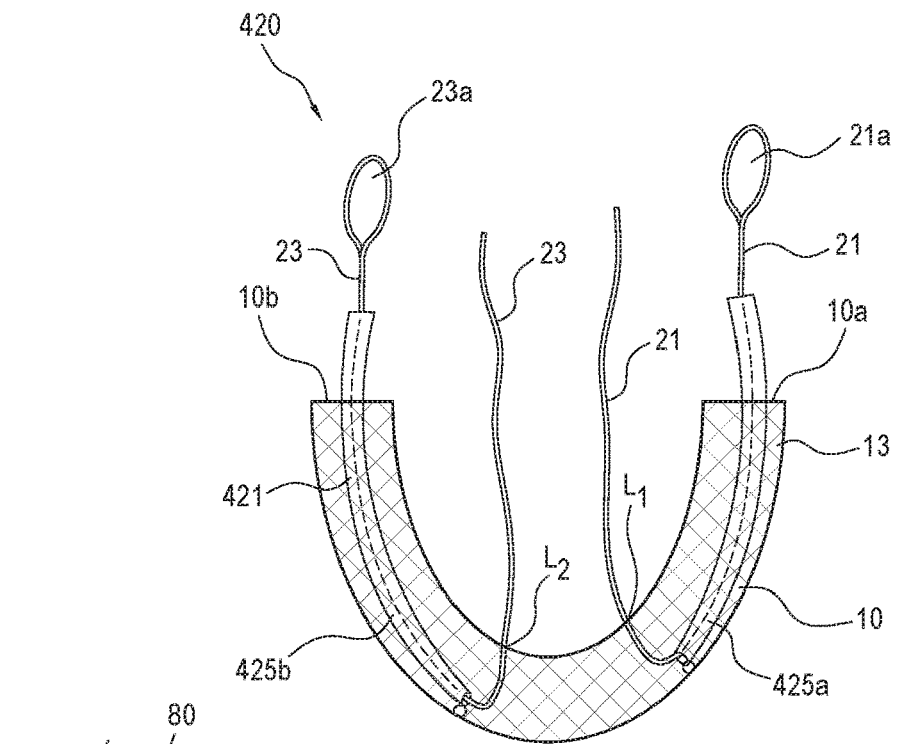
FIG. 17 illustrates a surgical construct according to another exemplary embodiment.
Figure 18:
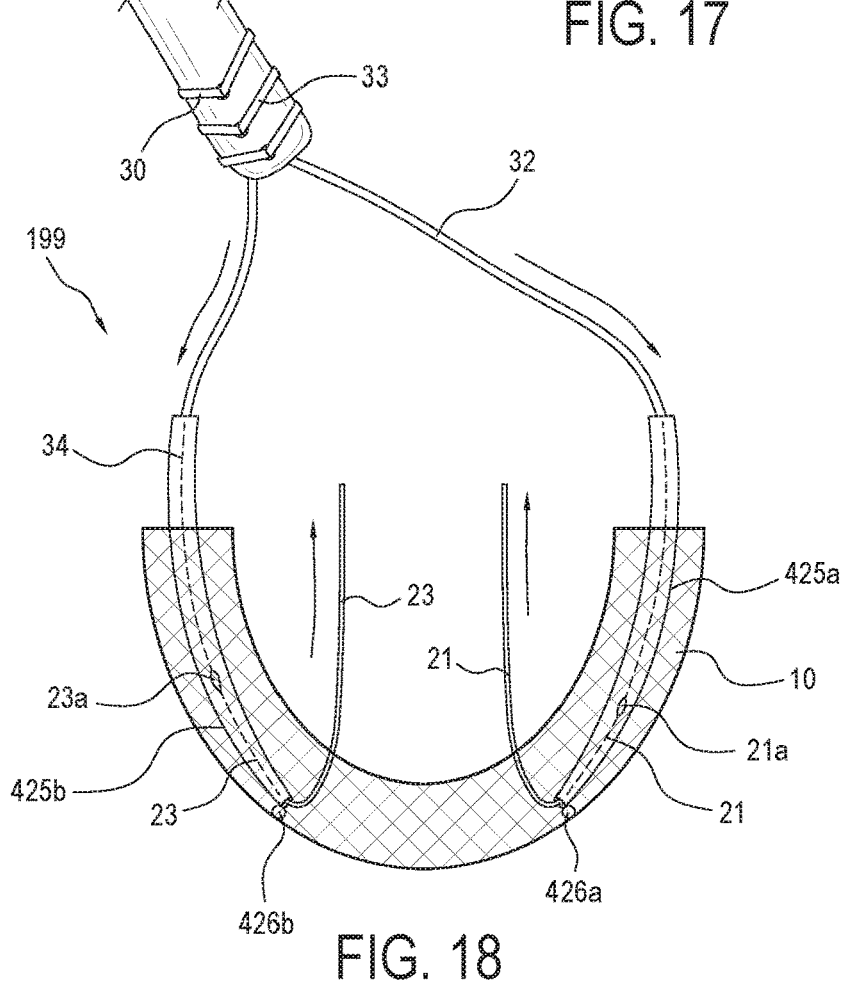
FIG. 18 illustrates the surgical construct of FIG. 17 attached to soft tissue.

Referring now to the drawings, where like elements are designated by like reference numerals, FIGS. 1-4 illustrate surgical construct 20 (soft anchor 20; knotless soft anchor construct 20; construct 20; knotless surgical construct 20) employed in the formation of surgical assembly 99 (FIG. 4) of the present disclosure. FIGS. 5-13 illustrate steps of tissue repair 101 with exemplary surgical construct 20 and assembly 99 of FIGS. 1-4. FIG. 14 illustrates another exemplary construct 120 of the present disclosure. FIGS. 15-17 illustrate yet additional exemplary constructs 220, 320, 420 of the present disclosure. FIG. 18 illustrates the exemplary construct 420 of FIG. 17 attached to soft tissue.

FIG. 1 illustrates exemplary surgical construct 20 which includes a soft anchor sleeve 10 (sheath 10; sleeve 10; tubular member 10; tube 10) with a body 13 and one or more flexible materials or flexible strands 21, 23 extending through at least an inner portion of the body 13. Soft anchor sleeve 10 is provided with a first end 10a and a second end 10b. At least one of the first and second ends 10a, 10b may be an open end.

In an exemplary embodiment, flexible strands 21, 23 are shuttling devices (passing devices or shuttle/pull devices or suture passers such as shuttling wires or sliding shuttle stitches) attached to the soft anchor sleeve 10. Flexible strands 21, 23 may be shuttling devices with a small closed loop 21a, 23a at one end, employed to shuttle/pass additional flexible strands through the sleeve 10, as detailed below. The shuttling devices 21, 23 may be shuttling wires or sliding shuttle stitches. The shuttling devices 21, 23 may be loaded with the flexible strands.

In the exemplary embodiment of FIG. 1, surgical construct 20 includes soft anchor sleeve 10 in the form of a tubular member with a first end 10a and a second end 10b, and two exemplary flexible shuttling devices 21, 23 (first and second shuttling devices 21, 23) exiting each of the first end 10a and the second end 10b of the soft anchor sleeve 10, and oriented in opposite directions, i.e., loop 21a is located on one end opposite to the end where loop 23a is located. The two shuttling devices 21, 23 may extend through the body 13 of sleeve 10 (for example, through one or two passages within the body 13) in various directions and/or orientations and/or at various locations throughout a length of the sleeve 10. For example, and as shown in FIG. 1, the two shuttling devices may be passed in opposite directions and in a side-by-side configuration relative to longitudinal axis 13a of the sleeve 10.

Figure 2:
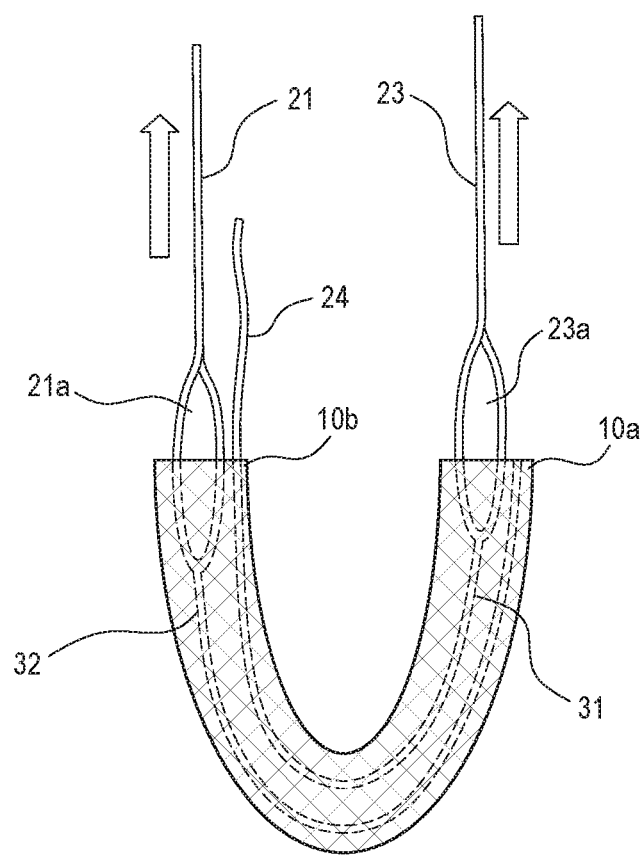
FIG. 2 illustrates the surgical construct of FIG. 1 employed to shuttle flexible strands.

The first and second shuttling devices 21, 23 are configured to be pulled out of the body of the soft anchor sleeve to allow first and second flexible strands 32, 34 to pass through the body 13 of the sleeve 10, as shown in FIG. 2.

Figure 3:
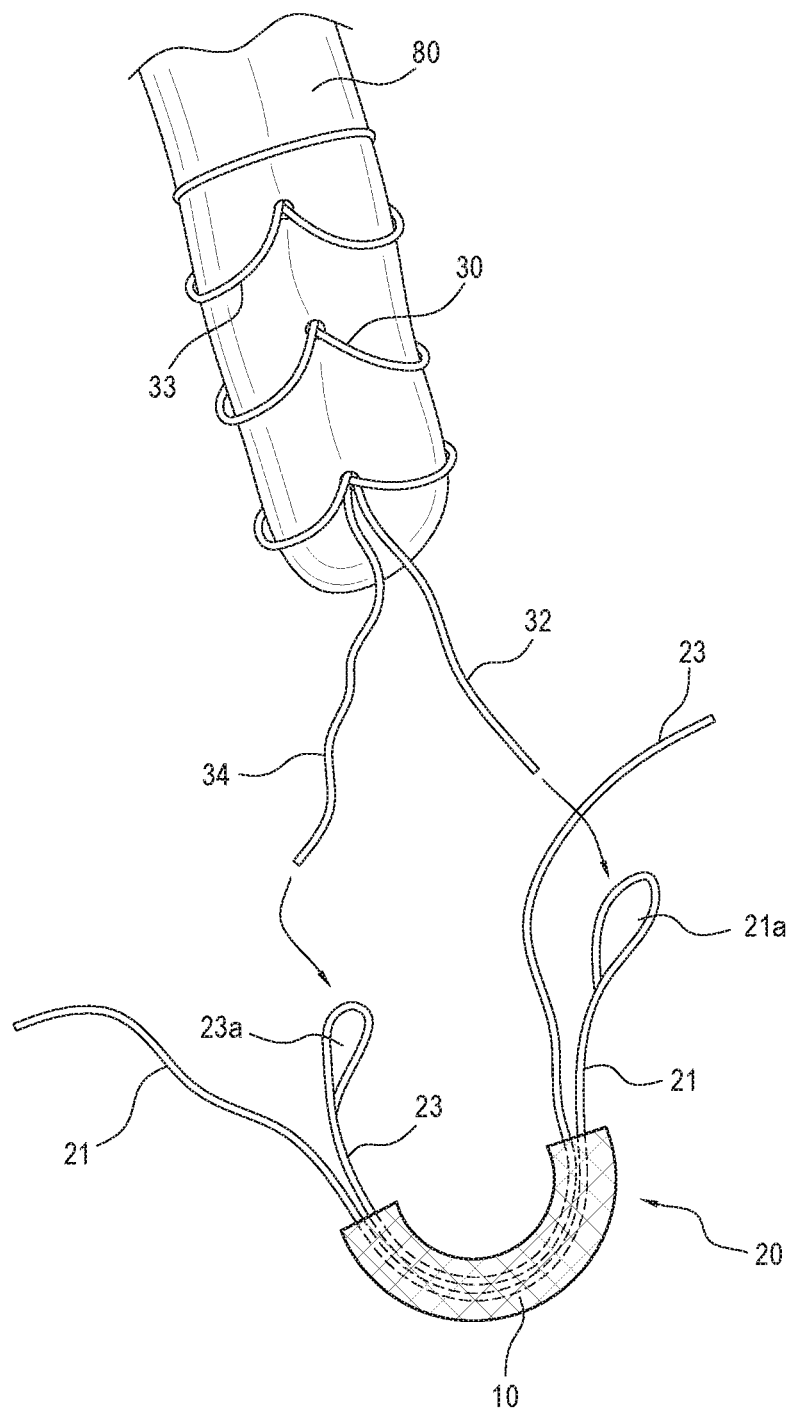

FIG. 3 illustrates construct 20 of FIG. 1 in the vicinity of tendon 80 which has been sutured (for example, whipstitched) with flexible strand 30 to form sutured region 33 and two flexible first and second free ends 32, 34 (first and second limbs 32, 34; first and second flexible strands 32, 34; first and second sutures 32, 34) extending away from region 33. First end 32 is passed through loop 21a of first shuttling device 21. Second end 34 is passed through loop 23a of second shuttling device 23. Once the first and second shuttling devices 21, 23 are pulled out of the body 13 of sleeve 10, the first and second flexible strands 32, 34 (which are attached to stitched tendon 80 yet are free, flexible ends) are pulled into the body 13 of the sleeve 10, oriented in opposite directions and locations, and extending in a direction about parallel to longitudinal axis 13a of sleeve 10, to obtain surgical assembly 99, shown in FIG. 4 First and second shuttling devices 21, 23 may be pulled out of the body 13 of sleeve 10 simultaneously or sequentially.

Surgical assembly 99 is a tensionable construct 99. Pulling on the ends 32, 34 in the directions of arrows A1, A2 (FIG. 4) allows approximation of distal end 83 of tendon 80 relative to the body 13 of surgical sleeve 10. Passing of the limbs 32, 34 of the flexible material/strand 30 within the flexible sleeve 10 forms tensionable construct 99 which includes at least one adjustable closed loop 55 (self-locking mechanism 55) that allows the user (for example, surgeon) to control the tension of the flexible strand 30 on first tissue 80 (soft tissue) to be attached to a second tissue 90 (for example, bone). Loop 55 may be knotless or knotted.

Exemplary surgical assembly 99 is a double-tail construct with two flexible sutures. However, additional embodiments wherein one or three or more flexible sutures are provided along a length of the sleeve 10 are also contemplated. The number of flexible sutures of tensionable construct 99 will depend on the number of sutures employed to fixate/secure tendon 80, for example, to suture/stitch distal end 83 of tendon 80.

FIGS. 5-13 illustrate exemplary steps of a method of distal biceps tendon repair using the surgical assembly 99 with surgical construct 20 and a tension-slide technique. The method allows the surgeon to tension and repair the biceps tendon through a single anterior incision. The combination of the soft cortical button/sleeve fixation coupled with an interference screw creates a strong, anatomic repair.

Surgical Technique

Place the patient in a supine position on the operating room table. Make transverse incision approximately few centimeters distal to the elbow flexion crease. Identify the lateral antebrachial cutaneous nerve and retract it laterally. Identify the retracted distal end of the biceps tendon and deliver it through the incision. Debride the end of the tendon to remove any degenerative or diseased tissue. The tendon 80 could pass through a sizing block to ensure that it will fit through a bone tunnel. Whipstitch a portion (about 2.5 cm) of the distal end 83 of the biceps tendon 80 using a FiberLoop®, making sure to lock the sutures 30 by making the final pass proximal to the previous pass, to obtain stitched region 33. Cut the FiberLoop® near the needle, ensuring adequate length suture limbs 32, 34. Mark a line on the tendon 1 cm from the end to help visualize the tendon docking into the radial tuberosity.

Thread one limb 32 of suture 30 through loop 21a of first shuttling device 21, and thread one limb 34 of suture 30 through loop 23a of second shuttling device 23. Pull on each shuttling device simultaneously to ensure that the sutures 32, 34 are passed through the body 13 of sleeve 10 and slide freely within the sleeve, and to obtain assembly 99.

FIG. 5

With the elbow in full extension and full supination, expose the radial tuberosity and debride it of any remaining soft tissue. Drill a bi-cortical tunnel 91 through the radial tuberosity 90. Fluoroscopy may be used to confirm drill placement in the radial tuberosity.

FIGS. 6-8

Drill a uni-cortical tunnel 92 (FIG. 7) over the guide pin and remove both the pin and reamer. Tunnel 92 has a diameter smaller than about 8 mm.

Insert the surgical assembly 99 through both cortices of the radial tuberosity. Flexing the forearm may aid in sleeve and tendon insertion. Verify that the sleeve with both suture limbs 32, 34 is deployed through both cortices.

FIGS. 9 and 10

Pull on the free suture limbs 32, 34 to seat the sleeve 10 against the radius. Grasp each limb 32, 34 of suture 30 and slowly apply tension to dock the tendon 80 into the bone tunnel 92. The previously marked line may also aid in visual confirmation that the tendon is fully docked into the bone tunnel 92.

FIG. 11

Once the tendon 80 is fully seated, free needle may be used to pass one limb through the tendon 80 and tie a knot 88, using a knot pusher if necessary.

FIG. 12

Load fixation device 89 (for example, a 7 mm×10 mm PEEK tenodesis screw 89) onto a driver and load one suture limb through the driver. Insert the screw 89 on the radial side of the bone tunnel 92, pushing the tendon more ulnar. The screw 89 should seat flush with the anterior cortex.

FIG. 13

Tie the suture limbs over the screw to complete the repair 101.

FIG. 14 illustrates another exemplary multiple-loop construct 120. Surgical construct 120 is similar to surgical construct 20 of FIG. 1 but differs in that each of the shuttling devices 121, 123 has two shuttling loops 121a, 121b and 123a, 123b, respectively. Thus, surgical construct 120 is provided with four shuttling loops to aid in passing of multiple flexible strands, as desired. Each of the shuttling sutures have a loop on each end. This aspect allows the surgeon/user to choose how to load the sutures from the tendon (soft tissue)—either in opposite directions or shuttle the limbs through in the same direction.

Like surgical construct 20, surgical construct 120 is also provided with a soft anchor sleeve 10 (sheath 10; sleeve 10; tubular member 10) with a body 13 and at least one flexible material or flexible strand 121, 123 (shuttling devices 121, 123) extending through at least an inner portion of the body 13 and along a length of the body 13. Soft anchor sleeve 10 is provided with a first end 10a and a second end 10b. At least one of the first and second ends 10a, 10b may be an open end. In the exemplary embodiment shown in FIG. 14, the surgical construct 120 includes a soft anchor 10 (loadable soft button 10) in the form of a double-loaded suture construct.

FIGS. 15-17 illustrate additional exemplary constructs 220, 320, 420 of the present disclosure. Constructs 220, 320, 420 are about similar to surgical construct 20 of FIG. 1 in that they also include a soft anchor sleeve 10 (sheath 10; sleeve 10; tubular member 10; tube 10) with a body 13, and one or more flexible materials or flexible strands 21, 23 extending through at least an inner portion of the body 13. Like in the previously-described embodiments, flexible strands 21, 23 are shuttling devices (passing devices or shuttle/pull devices or suture passers such as shuttling wires or sliding shuttle stitches) attached to the soft anchor sleeve 10, and each provided with a small closed loop 21a, 23a at one end. The shuttling devices 21, 23 may be shuttling wires or sliding shuttle stitches. The shuttling devices 21, 23 may be loaded with the flexible strands.

In the exemplary embodiments of FIGS. 15-17, the exemplary flexible shuttling devices 21, 23 (first and second shuttling devices 21, 23) do not exit each of the first end 10a and the second end 10b of the soft anchor sleeve 10 (as in the previous embodiments), but are rather oriented at a 90 degree relative to the sheath 10 (construct 220 of FIG. 15), or longitudinal to the sheath 10 but exiting at about 90 degree angle (construct 320 of FIG. 16). In these embodiments, the sutures 32, 34 will be shuttled through the sheath 10 at about 90 degrees to the sheath (with construct 220), and longitudinal to the sheath 10 but exiting at a 90 degree angle relative to the sheath (with construct 320).

For example, FIG. 15 illustrates construct 220 with the shuttling devices 21, 23 each extending through sheath 10 for a length/distance "D" in a direction about parallel to transversal axis 13b of the sheath 10. Distance D may be about equal to a diameter of the sheath 10. None of the first and second shuttling devices 21, 23 enters any of the ends 10a, 10b of the sheath 10 in this specific exemplary embodiment. Rather, each of the shuttling devices 21, 23 enters and exits the sheath 10 at four different locations situated on an outer longitudinal side of the sheath 10. For example, shuttling device 21 enters and exits sheath 10 at locations F1, F2, F3, F4 situated on exterior surface 10f (outer surface 10f) of tubular sheath 10. Similarly, shuttling device 23 enters and exits the sheath 10 at four locations spaced apart from the locations F1, F2, F3, F4. The entry and exit points of the shuttling devices may be spaced apart relative to each other or may coincide (all or a part of them). In this exemplary embodiment, the shuttling devices (and the sutures to be shuttled with them) of construct 220 extend about perpendicular to the sheath (i.e., perpendicular to longitudinal axis 13*a* of the sheath 10).

FIG. 16 illustrates construct 320 with the shuttling devices 21, 23 each extending through sheath 10 for a length/distance "d" in a direction about parallel to the longitudinal axis 13*a*. First shuttling device 21 enters one of the ends 10*a*, 10*b* of the sheath 10 (for example, end 10*a*) and then exits the sheath at location L1 of the sheath. Location L1 is spaced apart from ends 10*a*, 10*b*. Similarly, second shuttling device 23 enters one of the ends 10*a*, 10*b* of the sheath 10 (for example, end 10*b*) and then exits the sheath at location L2 of the sheath. Location L2 is spaced apart from ends 10*a*, 10*b*. Locations L1 and L2 may be spaced apart from each other (as shown in FIG. 16) or may coincide (i.e., both limbs exit the sheath at a common point). In the specific embodiment of FIG. 16, shuttle sutures 21, 23 extend about longitudinal to the sheath 10 but exit the sheath at about 90 degrees. In this specific embodiment, the shuttling devices (and the sutures to be shuttled with them) extend longitudinal to the sheath (i.e., about parallel to longitudinal axis 13*a*) but exit at a 90 degree angle.

FIG. 17 illustrates yet another exemplary construct 420 of the present disclosure. Construct 420 is a knotless soft button construct (knotless soft button option) provided with a knotless mechanism (knotless cinching mechanism). In the previously-described embodiments, the shuttling sutures (passing sutures 21, 23) pull the sutures 32, 34 from the tendon 80 through and out of the sheath 10 and then both sutures 32, 34 may be tied together after the tendon 80 is pulled down into the bone hole, to complete the repair (i.e., the sutures 32, 34 are part of knotted constructs). As detailed below, construct 420 is a knotless construct in that sutures 32, 34 do not form a knot to complete the repair (as in the previously-described embodiments) but may be simply cut flush to achieve a knotless repair.

Construct 420 is about similar to surgical construct 320 detailed above in that it also includes a soft anchor sleeve 10 (sheath 10; sleeve 10; tubular member 10; tube 10) with a body 13, and one or more flexible materials or flexible strands 21, 23 extending through at least an inner portion of the body 13. Like in the previously-described embodiment, flexible strands 21, 23 are shuttling devices (passing devices or shuttle/pull devices or suture passers such as shuttling wires or sliding shuttle stitches) attached to the soft anchor sleeve 10, and each provided with a small closed loop 21*a*, 23*a* at one end. First shuttling device 21 enters one of the ends 10*a*, 10*b* of the sheath 10 (for example, end 10*a*) and then exits the sheath at location L1 of the sheath. Location L1 is spaced apart from ends 10*a*, 10*b*. Similarly, second shuttling device 23 enters one of the ends 10*a*, 10*b* of the sheath 10 (for example, end 10*b*) and then exits the sheath at location L2 of the sheath. Location L2 is spaced apart from ends 10*a*, 10*b*. Locations L1 and L2 may be spaced apart from each other (as shown in FIG. 17) or may coincide (i.e., both limbs 21, 23 and 32, 34 exit the sheath at a common point). In the specific embodiment of FIG. 17, shuttle sutures 21, 23 extend about longitudinal to the sheath 10 but exit the sheath at about 90 degrees.

Construct 420 also includes a knotless mechanism 421 which may be similar to the knotless SutureTak® self-locking technology ("finger trap" design). Knotless mechanism 421 is part of tensionable construct 199 (FIG. 18) and may be in the form of two additional flexible materials 425*a*, 425*b* that are attached to the main sheath 10 by various methods known in the art (for example, by sewing) to provide counter-traction for the finger trap. The suture limbs 32, 34 of the flexible strand 30 attached to tendon 80 (shown in FIG. 18) are passed through the loops 21*a*, 23*a* and then shuttled through the sheath 10 and knotless mechanism 421 to form tensionable construct 199. The suture limbs 32, 34 may be cut flush to obtain a knotless repair.

The knotless version shown in FIGS. 17 and 18 could include stuffed structures for flexible materials 425*a*, 425*b*, and these stuffed structures could be attached to the sheath by various methods, for example, sewing. The stuffing (stuffed structures) is preloaded onto the knotless mechanism; the limbs 32, 34 are pulled through the stuffed structures (by employing the shuttling devices) and stopped at the ends 426*a*, 426*b* of the stuffed structures 425*a*, 425*b*. Limbs 32, 34 may be braided suture or suture tape (such as Arthrex FiberWire® suture and Arthrex FiberTape®) that because of a greater diameter than the diameter of the shuttling device will be retained within the body of the stuffed structures 425*a*, 425*b* (flexible materials 425*a*, 425*b*). This allows the surgeon the option to reduce the tendon to the desired distance.

In additional embodiments, the length of suture 30 with limbs 32, 34 employed to suture/whipstitch tendon 80 may be engineered so that the surgeon whipstitches a certain length of it and then the limbs 32, 34 are pulled through the sheath 10 and locked within it, i.e., locked within stuffed structures 425*a*, 425*b* (flexible materials 425*a*, 425*b*) in a knotless manner. The flexible materials 425*a*, 425*b* may be any structures that allow the passage of limbs 32, 34 and locking of the limbs within the body of the flexible materials.

The first and second shuttling devices 21, 23, 121, 123 may be passing devices; shuttle/pull devices; suture passers such as shuttling wires or sliding shuttle stitches; or any combination of these devices. The shuttling devices are configured to be pulled out of the body of the soft anchor sleeve 10 to allow the suture strands to pass through the body of the sleeve and be further secured to another tissue (for example, bone). The plurality of flexible limbs/sutures that are shuttled/passed with the first and second shuttling devices 21, 23, 121, 123 may be shuttled simultaneously or sequentially. The soft anchor sleeve 10 may be secured to a first tissue (for example, bone) and the tensionable construct (formed by the soft tissue and attached suture strands) may secure a second tissue (for example, the soft tissue) to the first tissue.

The methods of the present disclosure are conducted by inserting flexible sleeve 10 (soft anchor sleeve, tubular member, or sheath 10) of surgical construct 20, 120, 220, 320, 420 in a hole 92 in bone 90; and fixing limbs of flexible material/strand 30 (attached to tissue 80) in or to the flexible sleeve 10 (soft anchor sleeve 10; tubular member 10) in a knotted or knotless manner. The limbs 32, 34 of the flexible material/strand 30 are passed within the flexible sleeve 10 to form tensionable construct 99, 199 which may include at least one adjustable closed loop 55 (self-locking mechanism 55) or knotless mechanism 421 and which allows the user (for example, surgeon) to control the tension of the flexible strand 30 on first tissue 80 (soft tissue) to be attached to a second tissue 90 (for example, bone).

The shuttling devices 21, 23, 121, 123 may be shuttle/pull suture devices such as shuttling wires or passing instruments, for example, a FiberLink™ or a Nitinol loop. Each of the shuttling devices 21, 23, 121, 123 may be provided loaded with flexible limbs of flexible strands 30. Each of the shuttling devices 21, 23, 121, 123 is configured to be pulled out of the body of the sheath 10, to allow limbs of the flexible strand 30 to pass through the body of the soft anchor sleeve. The passage of the limbs of the flexible strand may optionally form a knotless closed adjustable loop having an adjustable length and perimeter. Each of the shuttling devices 21, 23, 121, 123 may be provided with one, two, or more than two, shuttling eyelets or closed loops, to facilitate passing of multiple flexible strands/sutures through body 13 of sheath/sleeve 10. For example, two shuttling loops may be provided at one end of the shuttling device, whereas one loop may be provided at another end of the shuttling device (for example, the opposite end).

Flexible ends/limbs of flexible strand 30 are passed through shuttling loops or eyelets 21a, 23a, 21b, 23b of shuttling devices 21, 23, 121, 123. The shuttling devices 21, 23, 121, 123 are then pulled so that the flexible ends/limbs of suture 30 are brought inside the sheath 10 to form adjustable closed loop 55 of repair 101 (FIGS. 4 and 13) or knotless mechanism 421 (FIGS. 17 and 18). Loop 55 and/or knotless mechanism 421 are provided attached to tissue 80 to be secured to tissue 90 through soft anchor sleeve 10. Loop 55 and/or knotless mechanism 421 allow first tissue 80 to achieve the desired approximation relative to second tissue 90. Loop 55 and/or knotless mechanism 421 may be knotless or knotted.

Figure 4:
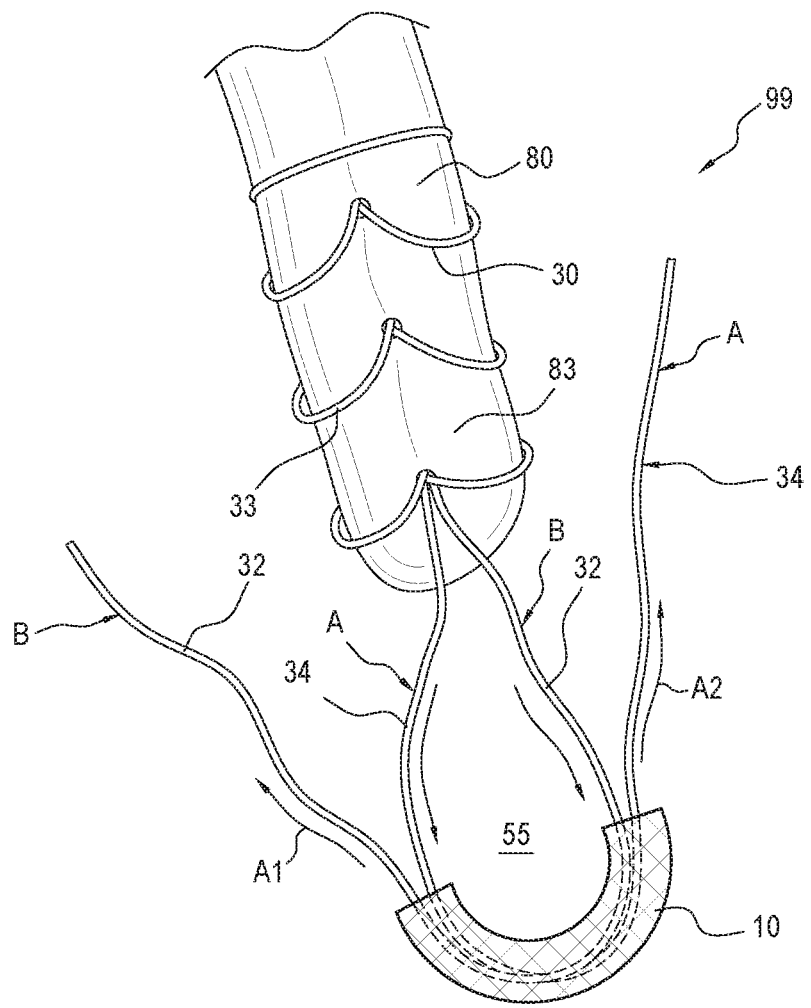
Figure 11:
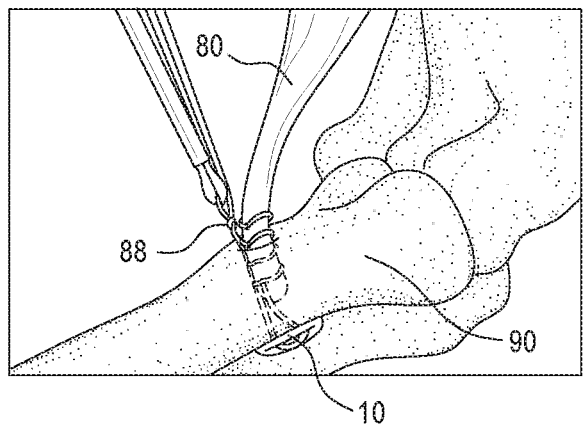
Figure 12:
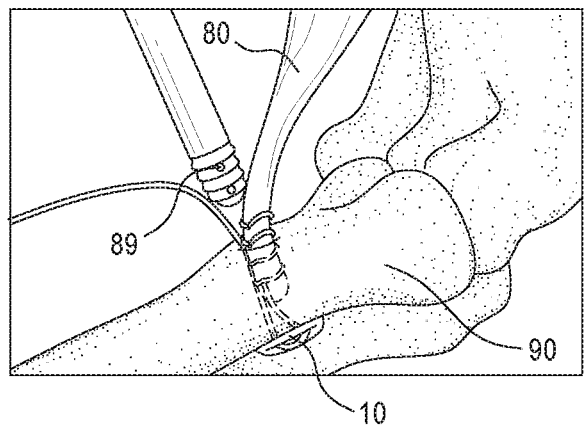
Figure 13:
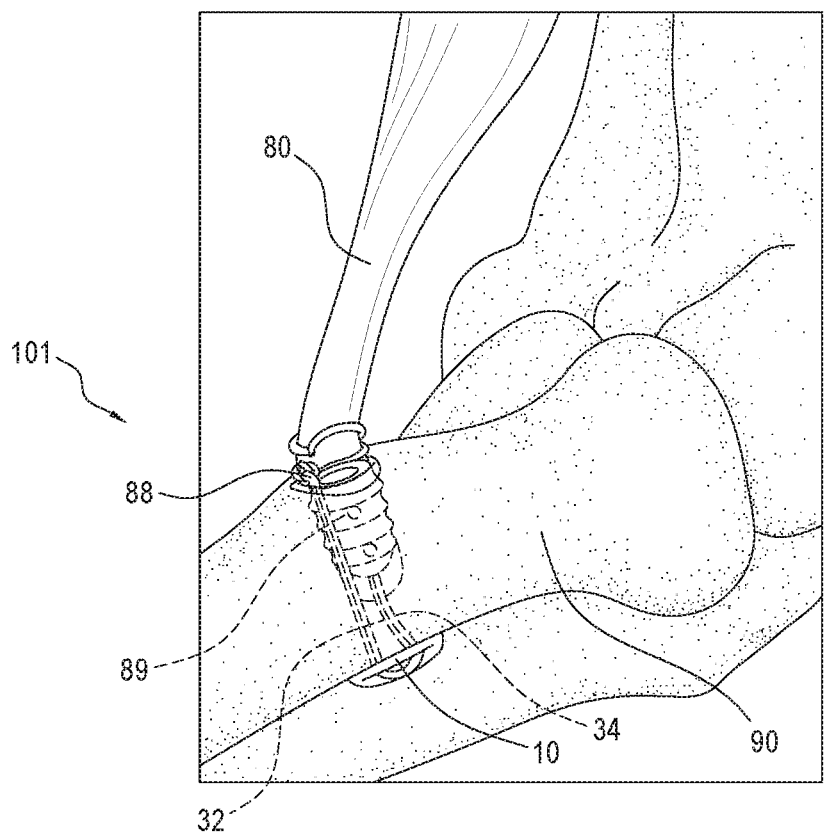

Suture limbs passed through the soft anchor sleeve 10 may exit the soft anchor sleeve 10 at various locations relative to ends 10a, 10b. For example, the suture limbs may exit the most distal and proximal ends (as shown in FIG. 4, for example) or at locations which are close to the ends 10a, 10b (spaced apart from ends 10a, 10b) as shown in FIGS. 15-18, for example. One flexible strand may enter the soft anchor sleeve through the first end 10a and may exit the anchor sleeve 10 at a location proximal the second end 10b of the soft anchor sleeve 10.

Flexible strands 30, 32, 34 and tensionable construct 99, 199 may be formed of flexible materials and strands such as suture (for example, round suture) or tape (for example, suture tape) or combination of suture and tape. The flexible strands may have cross-sections of various forms and geometries, including round, oval, rectangular, or flat, among others, or combination of such forms and geometries. In an exemplary embodiment only, at least one of flexible strands 30, 32, 34 may be provided as a cord or suture which may be braided, knitted or woven. Flexible strands 30, 32, 34 may be any tissue repair strands, for example, suture strands, nitinol strands, FiberLink™ or combinations of such materials, among many others.

Flexible strands 30, 32, 34 and/or sheath 10 may be made of any known suture construct, such as multifilament, braided, knitted, woven suture, or including fibers of ultra-high molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Flexible strands 30, 32, 34 and/or sheath 10 may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical constructs 20, 120, 220, 320, 420 can be used with any type of flexible material or suture known in the art. The strands 30, 32, 34 and/or sheath 10 may be also formed of a stiff material, or combination of stiff and flexible materials, depending on the intended application. The strands 30, 32, 34 and/or sheath 10 may be also coated and/or provided in different colors.

Flexible sheath 10 may be dimensioned to allow secure insertion and installing into an opening or tunnel or hole/socket within bone, so that the sheath is below a cortical surface of the bone. The constructs of the present disclosure are not limited to areas with good bone and depth, but could be also used for unicortical applications as well. Sheath design can be modified as needed while keeping the construct consistent based on repair location (sheath size or type). The construct creates a knotless repair, wherein the repair suture is fixed to soft tissue and then limbs of the repair suture are passed through the sheath, with both limbs passing from one end of the sheath to the other end of the sheath, and also extending through a bone tunnel.

Shuttling loops 21a, 23a, 21b, 23b of shuttling devices 21, 23, 121, 123 are flexible, continuous loops or eyelets that may have similar or different diameters and/or similar or different perimeters. Shuttling loops may be formed of nitinol or similar material (for example, alloy or metal). If a shuttling device is provided with two or more shuttling loops or eyelets, the eyelets may be all adjacent to each other (i.e., provided at a same end of the shuttling device and in sequential order), one after another spaced apart along a length of the shuttling device.

For multiple-tail constructs, the multiple flexible limbs may be passed through one of the two shuttling loops and then passed all simultaneously. For example, a first plurality of limbs (for example, two limbs) may be passed through loop 21a and a second plurality of limbs (for example, three limbs) may be passed through loop 21b in a single pass step.

Surgical constructs 20, 120, 220, 320, 420 may be preferably coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

In additional embodiments, sheath 10 may be formed of braided polyester with or without a core (as long as it allows passage of shuttling devices and flexible strands through it), and the flexible strands may be suture. If desired, at least one of the sheath 10 and/or flexible strand 30, 32, 34 may be coated, impregnated, or otherwise stiffened with a material such as plastic, for example. Preferably, flexible limbs of suturing construct may have a very fine end that is coated, impregnated, or stiffened with a material such as plastic, for example.

The sheath 10 and/or flexible strand 30, 32, 34 may be also provided with tinted tracing strands, or otherwise contrast visually with the sheath of the construct, which remains a plain, solid color, or displays a different tracing pattern, for example. Various structural elements of surgical constructs 20, 120, 220, 320, 420 and assembly 99, 199 (tensionable construct 99, 199) may be visually coded, making identification and handling of the suture legs simpler. Easy identification of suture in situ is advantageous in surgical procedures.

The surgical constructs and assemblies of the present disclosure have applicability to suture applications that may be employed in surgical procedures such as shoulder repairs, biceps repairs, and other reconstruction procedures, and applications for suture used in or with suture anchors.

An exemplary method of tissue repair may comprise inter alia the steps of installing a soft anchor 10 into or onto bone; and threading limbs 32, 34 of a suture 30 attached to tendon 80 through the soft anchor 10, to attach the tendon 80 to the soft anchor 10 in a knotted or knotless manner. The soft anchor 10 is a soft loadable button. The soft loadable button may be a knotted construct or a knotless construct.

An exemplary method of tissue repair may comprise inter alia the steps of (i) securing a soft anchor sheath 10 to a first tissue 90; (ii) passing a flexible strand 30 through or around a second tissue 80 to be secured to the first tissue; and (iii) securing limbs 32, 34 of the flexible strand 30 to the soft anchor sheath 10. The method may further comprise the step of passing limbs 32, 34 through a body of the sheath 10 by shuttling the limbs 32, 34 with at least one shuttling device. The method may further comprise the step of threading one of limbs 32, 34 through an eyelet of a shuttling device extending through at least a portion of the body of the sheath 10, and pulling the shuttling device to bring the one of the limbs 32, 34 within the body of the sheath. The method may further comprise the step of threading a first limb 32 through an eyelet 21a of a shuttling device 21 extending through at least a first portion of the body of the sheath 10; threading a second limb 32 through an eyelet 23a of a shuttling device 23 extending through at least a second portion of the body of the sheath 10; and pulling the shuttling devices 21, 23 to bring the limbs 32, 34 within the body of the sheath and form a tensionable construct 99, 199. The tensionable construct may be knotless or knotted.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of tissue repair comprising:
   installing a surgical construct into or onto bone, the surgical construct comprising a soft anchor sleeve or soft anchor sheath with a body, a longitudinal axis, a first end and a second end, and two shuttling devices attached to the soft anchor sleeve or soft anchor sheath, each of the two shuttling devices being provided with an eyelet to allow passing and shuttling of two corresponding flexible strands attached to soft tissue;
   attaching the flexible strands to the shuttling devices by passing each of the two flexible strands through the corresponding eyelet of each of the two shuttling devices; and
   passing the two flexible strands attached to the shuttling devices and to soft tissue, through the body of the soft anchor sleeve or soft anchor sheath and in opposite directions relative to the longitudinal axis of the soft anchor sleeve or soft anchor sheath, to form a tensionable construct and attach the soft tissue to the surgical construct.

2. The method of claim 1, wherein the tissue repair is a knotless tissue repair.

3. The method of claim 1, wherein the tissue repair is a knotted tissue repair.

4. The method of claim 1, wherein each of the shuttling devices extends through at least a portion of the body of the soft anchor sleeve or soft anchor sheath.

5. The method of claim 1, further comprising adjusting the length of the tensionable construct by pulling the flexible strands, to approximate the soft tissue to bone.

6. The method of claim 1, further comprising:
   installing the soft anchor sleeve or soft anchor sheath into a hole in the bone, or onto a cortex of the bone; and
   pulling on the shuttling devices to allow the two flexible strands to pass through the body of the soft anchor sleeve or soft anchor sheath, and to form the tensionable construct.

7. The method of claim 6, wherein the two flexible strands are passed simultaneously.

8. The method of claim 6, wherein the two flexible strands are passed sequentially.

9. The method of claim 6, wherein the shuttling devices extend along the longitudinal axis of the body, each of the shuttling devices being configured to be pulled out of the body of the soft anchor sleeve to allow the flexible strands to pass through the body of the soft anchor sleeve, to form the tensionable construct.

10. The method of claim 6, wherein the shuttling devices extend about parallel to a transversal axis of the body, each of the shuttling devices being configured to be pulled out of the body of the soft anchor sleeve to allow the flexible strands to pass through the body of the soft anchor sleeve, to form the tensionable construct.

11. The method of claim 1, wherein at least one of the soft anchor sleeve, the flexible strands, and the shuttling devices is visually coded.

12. The method of claim 1, wherein the soft tissue is distal biceps tendon and the bone is radial tuberosity.

13. The method of claim 1, wherein the tissue repair is knotted and further comprising securing the flexible strands to the bone by tying at least one knot.

* * * * *